US007629993B2

(12) United States Patent
Harless et al.

(10) Patent No.: US 7,629,993 B2
(45) Date of Patent: Dec. 8, 2009

(54) AUTOMATED WAFER DEFECT INSPECTION SYSTEM USING BACKSIDE ILLUMINATION

(75) Inventors: Mark Harless, Plymouth, MN (US);
Jeremy Jenum, Plymouth, MN (US);
Willard Charles Raymond, Plymouth, MN (US)

(73) Assignee: Rudolph Technologies, Inc., Flanders, NJ (US)

( * ) Notice: Subject to any disclaimer, the term of this patent is extended or adjusted under 35 U.S.C. 154(b) by 372 days.

(21) Appl. No.: 10/262,173

(22) Filed: Sep. 30, 2002

(65) Prior Publication Data
US 2004/0061779 A1 Apr. 1, 2004

(51) Int. Cl.
*H04N 9/47* (2006.01)
(52) U.S. Cl. ......................................... 348/126; 348/76
(58) Field of Classification Search ................. 348/125, 348/126, 76; 382/145, 149; 73/105; 356/237.4
See application file for complete search history.

(56) References Cited

U.S. PATENT DOCUMENTS

| 3,963,354 | A | | 6/1976 | Feldman et al. |
| 4,148,065 | A | | 4/1979 | Nakagawa et al. |
| 4,209,257 | A | | 6/1980 | Uchiyama et al. |
| 4,527,070 | A | | 7/1985 | Matsui et al. |
| 5,095,204 | A | | 3/1992 | Novini |
| 5,539,514 | A | * | 7/1996 | Shishido et al. .......... 356/237.4 |
| 5,737,072 | A | | 4/1998 | Emery et al. |
| 5,892,579 | A | | 4/1999 | Elyasaf et al. |
| 6,084,716 | A | | 7/2000 | Sanada et al. |
| 6,324,298 | B1 | * | 11/2001 | O'Dell et al. ................ 382/149 |
| 6,779,386 | B2 | * | 8/2004 | Neo et al. ...................... 73/105 |

* cited by examiner

*Primary Examiner*—Gims S Philippe
(74) *Attorney, Agent, or Firm*—Dicke, Billig & Czaja, PLLC

(57) ABSTRACT

A defect inspection system for the semiconductor and microelectronics industry. More particularly, the present invention relates to an automated defect inspection system for wafers or other semiconductor or electronic substrates of any kind or type that are transparent, translucent, opaque or otherwise capable of allowing at least some light to pass through.

16 Claims, 4 Drawing Sheets

AUTOMATED WAFER DEFECT INSPECTION SYSTEM USING BACKSIDE ILLUMINATION

BACKGROUND OF THE INVENTION

1. Technical Field

The present invention relates to defect inspection systems for the semiconductor industry. More particularly, the present invention relates to an automated defect inspection system for wafers or other semiconductor or electronic substrates of any kind or type that are transparent, opaque or otherwise capable of allowing at least some visible light to pass through.

2. Background Information

Over the past several decades, the semiconductor has exponentially grown in use and popularity. The semiconductor has in effect revolutionized society by introducing computers, electronic advances, and generally revolutionizing many previously difficult, expensive and/or time consuming mechanical processes into simplistic and quick electronic processes. This boom in semiconductors has been fueled by an insatiable desire by business and individuals for computers and electronics, and more particularly, faster, more advanced computers and electronics whether it be on an assembly line, on test equipment in a lab, on the personal computer at one's desk, or in the home electronics and toys.

The manufacturers of semiconductors have made vast improvements in end product quality, speed and performance as well as in manufacturing process quality, speed and performance. However, there continues to be demand for faster, more reliable and higher performing semiconductors.

One process that has evolved over the past decade or so is the semiconductor inspection process. The merit in inspecting semiconductors throughout the manufacturing process is obvious in that bad wafers may be removed at the various steps rather than processed to completion only to find out a defect exists either by end inspection or by failure during use.

Certain wafers are transparent, translucent, opaque or otherwise capable of transmitting light therethrough. Also, some silicon (not transparent or opaque) have through holes or mask properties that allow visible light to be transmitted through certain portions. These wafers that are transparent or opaque are generally made of type III-V or II-VI compounds and include gallium arsenide, indium phosphide, silicon carbide, and other non-silicon based substrates. These wafers may also be glass or oxide based which includes quartz and fused silica compounds.

Often these transparent or opaque wafers contain features on the back side (the side against the plate or stage) or inside the wafer that it is desirable to inspect. In some scenarios, brightfield or darkfield illumination as is disclosed below in the incorporated by reference August Technology patent applications, is sufficient to illuminate the wafers for inspection even where the features are on the backside or inside. However, in certain wafers, backside illumination is desirable or necessary to better illuminate the features to be inspected.

It is this need that the present invention addresses.

SUMMARY OF THE INVENTION

Specifically, the present invention is an automated method of inspecting a semiconductor wafer or microelectronic substrate in any form, size and shape where the wafer is transparent, opaque or otherwise capable (such as via holes) of transmitting at least some light therethrough where the invention includes a backside illumination system for illuminating the wafer or substrate from the backside for inspection from the front side of features on the back side or within the wafer or substrate.

BRIEF DESCRIPTION OF THE DRAWINGS

Preferred embodiment of the invention, illustrative of the best mode in which applicant has contemplated applying the principles, are set forth in the following description and are shown in the drawings and are particularly and distinctly pointed out and set forth in the appended claims.

Similar numerals refer to similar parts throughout the drawings.

DETAILED DESCRIPTION OF THE PREFERRED EMBODIMENT

Figure 1:
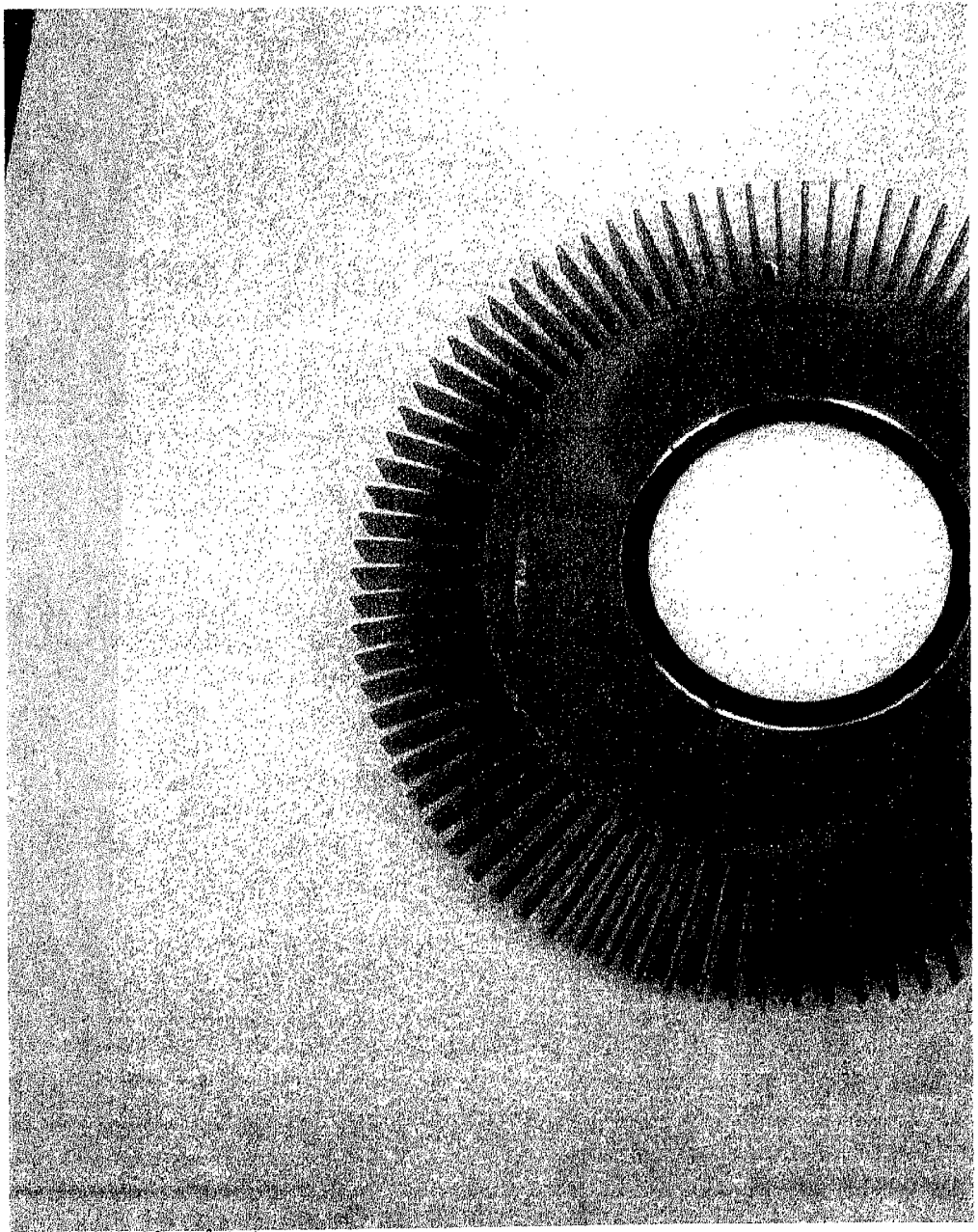
FIG. 1 is a top perspective view of one embodiment of the system.
Figure 2:
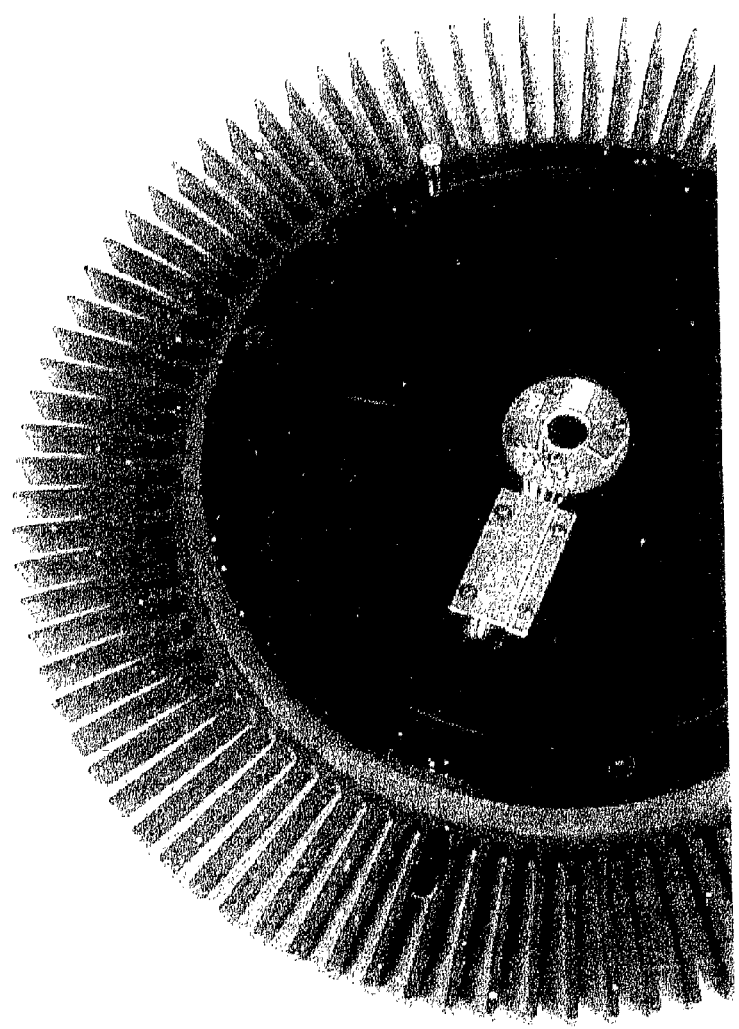
FIG. 2 is a bottom perspective view of the system of FIG. 1.
Figure 4:
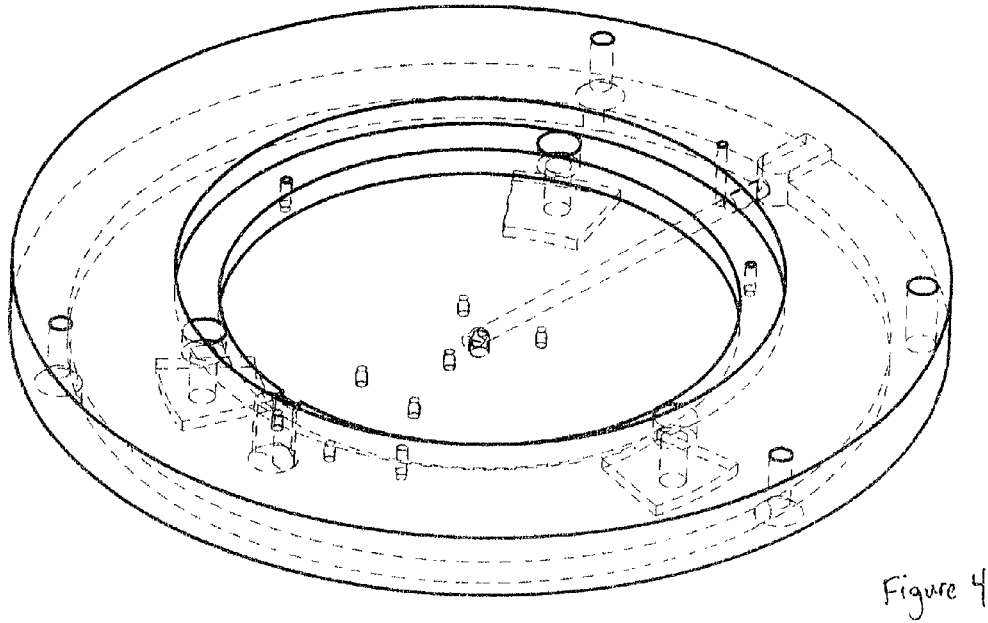
FIG. 4 is a view of the heat sink.
Figure 3:
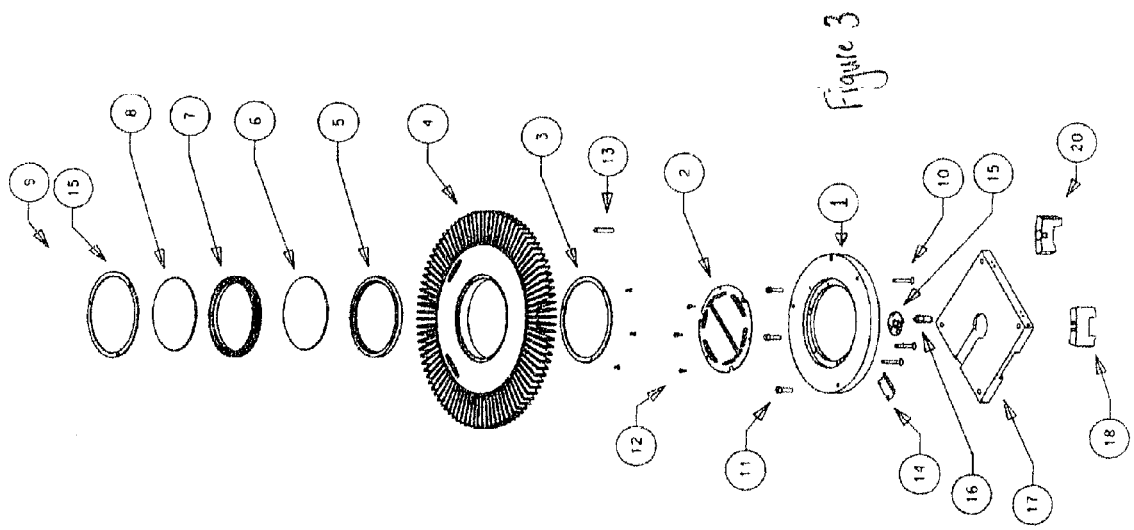
FIG. 3 is an exploded assembly view of the system of FIGS. 1-2.
Figure 5:
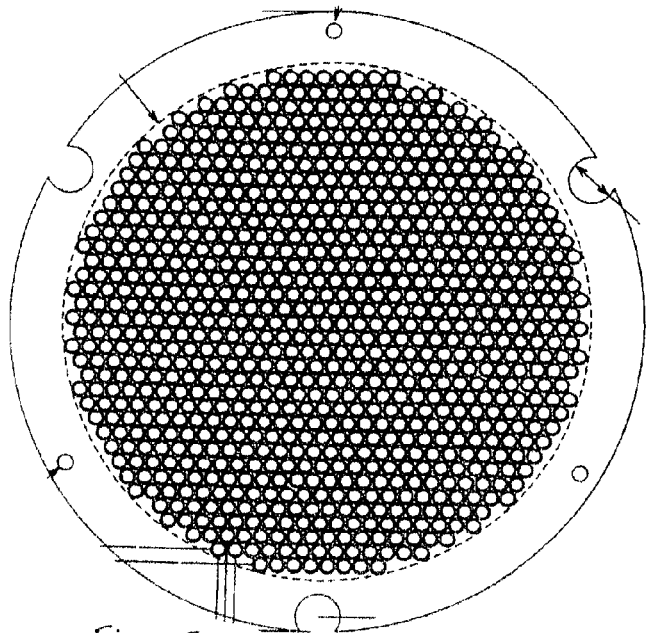
FIG. 5 is a top view of the LED assembly.
Figure 6:
FIG. 6 is a side view of the LED assembly.
Figure 7:
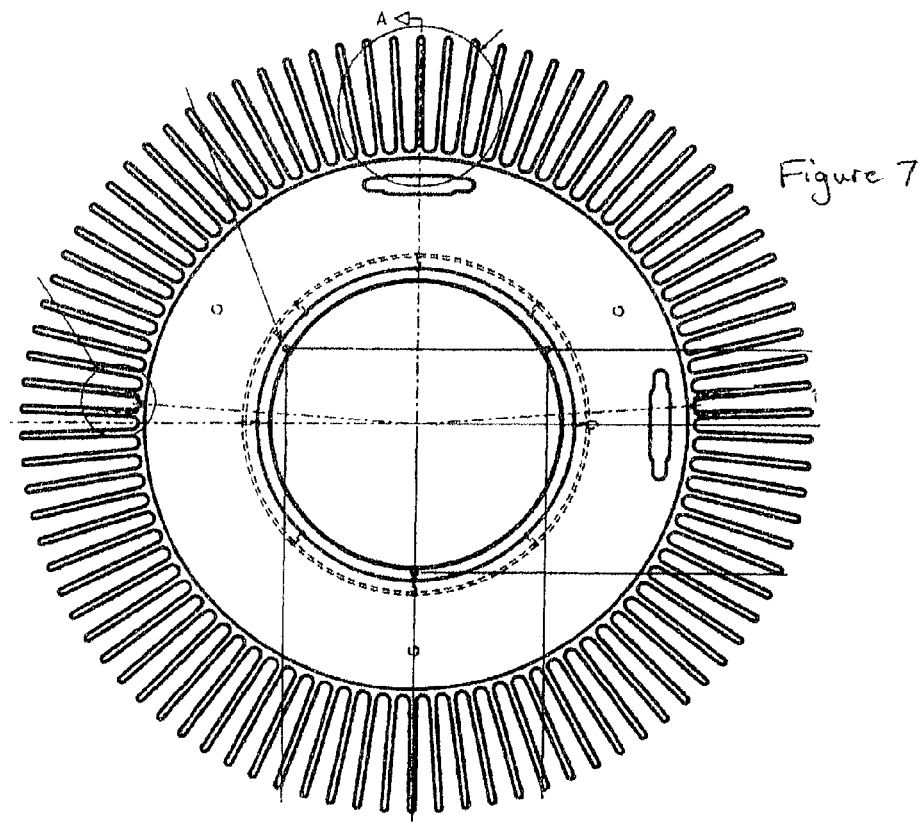
FIG. 7 is a top view of the radiator.

The present invention is a backside illumination system for illuminating the backside of semiconductor or microelectronic wafers or substrates where the wafers or substrates are transparent, translucent, opaque or otherwise capable of transmitting at least some of the illumination through the wafer or substrate to illuminating features therein, thereon the backside, or associated therewith. This invention is designed to be useful with any inspection process, including for example the automated defect inspection system described in commonly owned U.S. Provisional Application Nos. 60/092,923 and 60/092,701, filed on Jul. 15, 1998, and U.S. patent application Ser. No. 09/352,564, filed on Jul. 13, 1999, all of which are hereby incorporated by reference such that the backside illumination allows for inspection and viewing of the features on the backside or within the wafer from the front side.

The backside illumination system is indicated generally as S as is shown in the Figures. The system includes a heat sink 1, a light assembly 2, a clamp ring 3, a radiator 4, a diffuser ring 5, a diffuser glass 6, a top ring 7, a top or opal glass 8, a plurality of fasteners 9-12, a stop pin 13, a wire cover 14, a connector board assembly 15, a rotatable air fitting 16, a base 17, a hardstop 18, a sensor mount bracket 19, a hardstop back 20, and a power wire assembly 21.

Heat sink 1 is preferably an aluminum heat sink for dissipating heat from the backside illumination system and specifically the light assembly. The heat sink 1 in the preferred embodiment includes a center hole for receiving the light assembly where the light assembly seats on a ledge therein.

Light assembly 2 is any form of light for illumination. In the preferred embodiment, the light assembly 2 is a LED assembly including a plurality of LEDs or light emitting diodes. In this preferred design, the LEDs are arranged in a circular array format as is shown in the Figures whereby the LEDs are arranged to maximize the number provided.

Clamp ring 3 is a ring for securing or clamping the light assembly 2 to the heat sink 1. The light assembly is seated on the ledge in the heat sink and then the clamp ring secures it in place.

Radiator 4 is designed to radiate heat away from the light assembly. The light assembly when embodied as an LED assembly with tens, hundreds, or even thousands of LEDs creates significant heat. The heat sink functions to dissipate the heat away from the LED assembly. The radiator in turn functions to radiate this heat to the atmosphere. As a result, the radiator needs to be of a radial fin design as is shown in the Figures so as to provide maximum surface area to best radiate off the significant heat created by the LED assembly.

Diffuser glass 6 and the diffuser ring 5 that secures the glass in the radiator 4 are provided to diffuse the LED light radiating from the LEDs into a more even or diffuse pattern.

Top glass 8 and the top ring 7 that secures the glass in the radiator are provided as a top surface. It is on this surface that the wafers are inspected.

The system S provides illumination on the back side of a wafer or substrate while sitting on an inspection plate or stage. Other illumination such as brightfield or darkfield may also be provided. This backside illumination provides high intensity visible light that illuminates through either (1) a silicon wafer or substrate with light passages therein, or (2) a non-silicon wafer or substrate made of glass or a type III-V or II-VI compound such as gallium arsenide, indium phosphide, silicon carbide, or oxide based materials which includes quartz and fused silica compounds. This allows for viewing from the top or front side of features on the backside or within the wafer or substrate.

Accordingly, the invention as described above and understood by one of skill in the art is simplified, provides an effective, safe, inexpensive, and efficient device, system and process which achieves all the enumerated objectives, provides for eliminating difficulties encountered with prior devices, systems and processes, and solves problems and obtains new results in the art.

In the foregoing description, certain terms have been used for brevity, clearness and understanding; but no unnecessary limitations are to be implied therefrom beyond the requirement of the prior art, because such terms are used for descriptive purposes and are intended to be broadly construed.

Moreover, the invention's description and illustration is by way of example, and the invention's scope is not limited to the exact details shown or described.

Having now described the features, discoveries and principles of the invention, the manner in which it is constructed and used, the characteristics of the construction, and the advantageous, new and useful results obtained; the new and useful structures, devices, elements, arrangements, parts and combinations, are set forth in the appended claims.

What is claimed is:

1. An inspection system for inspecting or viewing wafers or substrates, the inspection system comprising:
    a backside illumination system defining a top surface from which illumination is directed to wafers or substrates being viewed or inspected, the wafers or substrates having a top side and a back side, the back side on the top surface;
    a radiator provided with the backside illumination system and including a plurality of radially projecting fins, the radiator for radiating heat generated by the backside illumination system to an atmosphere; and
    a camera for viewing or inspecting such wafers or substrates, the camera positioned above the top surface of the backside illumination system to receive illumination provided from the top surface through the wafer or substrate.

2. The inspection system of claim 1, wherein the radiator has a central aperture and the backside illumination system further comprises:
    a light assembly for generating the illumination, the light assembly secured relative to the radiator such that the illumination is directed through the central aperture.

3. The inspection system of claim 1, wherein the backside illumination system further comprises:
    a top glass defining at least a portion of the top surface of backside illumination system, the top glass secured in the central aperture of the radiator.

4. The inspection system of claim 3, wherein the backside illumination system is configured to support the wafers or substrates to be viewed or inspected on the top glass.

5. An inspection for inspecting or viewing wafers or substrates, the inspection system comprising:
    a backside illumination system defining a top surface from which illumination is directed to wafers or substrates being viewed or inspected, the wafers or substrates having a top side and a back side, the back side on the top surface, the backside illumination system including:
        a light assembly that generates light and heat when illuminating; and
        a heat sink for dissipating the heat from the light assembly, the heat sink having a center hole for receiving the light assembly;
        wherein the light assembly is seated in the center hole; and
    a camera for viewing or inspecting such wafers or substrates, the camera positioned above the top surface of the backside illumination system to receive illumination provided from the top surface through the wafer or substrate.

6. The inspection system of claim 5, wherein the light assembly is an LED assembly including a plurality of LEDs.

7. The inspection system of claim 6, wherein the plurality of LEDs are arranged in a circular array format.

8. The inspection system of claim 5, wherein the heat sink is substantially annular in shape.

9. The inspection system of claim 5, wherein the backside illumination system further comprises:
    a radiator including a plurality of radially projecting fins, the radiator mounted to the heat sink.

10. The inspection system of claim 9, wherein the radiator includes a central aperture coaxially aligned with the center hole of the heat sink such that light from the light assembly is transmitted through the central aperture.

11. The inspection system of claim 10, wherein the backside illumination system further comprises:
    a diffuser glass secured in the central aperture of the radiator to diffuse light from the light assembly.

12. A method of inspecting or viewing wafers or substrates, the method comprising:
    providing an illumination system defining a top surface from which illumination is provided;
    supporting a wafer or substrate with the top surface of the illumination system, the wafer or substrate having a top side and a back side;
    illuminating the back side of the wafer or substrate with illumination from the illumination system;
    providing a camera; and
    receiving the illumination from the illumination system from the top surface of the wafer with the camera;
    wherein the wafer or substrate is substantially free of light passages, the wafer or substrate is formed of at least one of a glass, a type II-V compound, a type II-VI compound, and an oxide-based material.

13. The method of claim 12, wherein the wafer or substrate transmits high-intensity, visible light.

14. The method of claim 12, wherein the wafer or substrate has light passages therein.

15. The method of claim 12, wherein the illumination from the illumination system is high-intensity, visible light.

16. The method of claim 12, wherein receiving the illumination from the illumination system with the camera includes viewing or inspecting features within the wafer or substrate with the camera using the illumination from the illumination system.

* * * * *

UNITED STATES PATENT AND TRADEMARK OFFICE
CERTIFICATE OF CORRECTION

PATENT NO. : 7,629,993 B2 Page 1 of 1
APPLICATION NO. : 10/262173
DATED : December 8, 2009
INVENTOR(S) : Harless et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2125 days.

Signed and Sealed this

Second Day of November, 2010

David J. Kappos
*Director of the United States Patent and Trademark Office*